United States Patent
Boyer et al.

(10) Patent No.: US 8,407,578 B2
(45) Date of Patent: Mar. 26, 2013

(54) CHEMICAL WEB BROWSER

(75) Inventors: Stephen K Boyer, San Jose, CA (US); James Rhodes, Hawthorne, NY (US)

(73) Assignee: International Business Machines Corporation, Armonk, NY (US)

( * ) Notice: Subject to any disclaimer, the term of this patent is extended or adjusted under 35 U.S.C. 154(b) by 356 days.

(21) Appl. No.: 12/565,001

(22) Filed: Sep. 23, 2009

(65) Prior Publication Data
US 2011/0072339 A1    Mar. 24, 2011

(51) Int. Cl.
*G06F 17/27*    (2006.01)

(52) U.S. Cl. ............................................ 715/212
(58) Field of Classification Search ............ 715/212
See application file for complete search history.

(56) References Cited

U.S. PATENT DOCUMENTS

| | | | |
|---|---|---|---|
| 5,953,720 A | | 9/1999 | Mithal et al. |
| 6,584,412 B1 * | | 6/2003 | Brecher ............... 702/27 |
| 6,792,426 B2 | | 9/2004 | Baumeister et al. |
| 7,337,013 B2 | | 2/2008 | Dove et al. |
| 7,924,270 B2 * | | 4/2011 | Phelan et al. ........... 345/173 |
| 8,046,212 B1 * | | 10/2011 | Hlava et al. ............. 704/7 |
| 2004/0073558 A1 | | 4/2004 | Schrijvers et al. |
| 2007/0226614 A1 * | | 9/2007 | Lorenzen et al. ........ 715/530 |

OTHER PUBLICATIONS

Agosti, et al., "A Formal Model of Annotations of Digital Content", ACM Transactions on Information Systems, vol. 26, No. 1, Article 3, Nov. 2007.
Hanus, Michael, "Type-Oriented Construction of Web User Interfaces", Principle and Practice of Declarative Programming, Jul. 10-12, 2006, Venice Italy.
Mills-Tettey, et al., "The Abels System: Designing an Adaptable Interface for Linking Simulations", Proceedings of the 2002 Winter Simulation Conference.

* cited by examiner

*Primary Examiner* — Laurie Ries
*Assistant Examiner* — Tionna Smith
(74) *Attorney, Agent, or Firm* — Andrea Bauer; Hoffman Warnick LLC

(57) ABSTRACT

The present invention relates to a system, method and program product for a chemical web browser. A chemical web browser including a document system for accessing a document containing at least one chemical name is provided. A chemical annotation system identifies the at least one chemical name within the document. A chemical formulae conversion system associates a chemical structure with the identified chemical name. The chemical structure is displayed.

20 Claims, 7 Drawing Sheets a) (2P/4S)-4-[4-Amino-5-(4-benzyloxy-phenyl)pyrrolo[2,3-d]pyrimidin-7-yl]-2-hydroxymethyl-pyrrolidine-1-carboxylic acid tert-butyl ester prepared analogously to Example 18 starting from (2R/4S)-4-[4-amino-5-(4-benzyloxy-phenyl)-pyrrolo[2,3-d]pyrimidin-7-yl]-pyrrolidine-1,2-dicarboxylic acid 1-tert-butyl ester 2-ethyl ester (Example 20a). 1 H-NMR (CDCl3, ppm): 8.52 (s, 1H), 7.52-7.32 (m, 7H), 7.1 (d, 2H), 6.95 (d,1 H), 5.50 (m, 1H), 5.13 (s, 2H), 4.62-4.42 (m, 2H), 4.28 (m, 2H), 4.10 (m, 1H), 3.95-3.70 (m, 1H), 2.75 (m, 1H), 2.50 (m, 1H),1.49 (s, 9H).

b) (2R/4S)-{4-[4-Amino-5-(4-benzyloxy-phenyl)-pyrrolo[2,3-d]pyrimidin-7-yl]-pyrrolidin-2-yl}-methanol: 0.100 g of (2R/4S)4-[4-amino-5-(4-benzyloxy-phenyl)-pyrrolo[2,3-d]pyrimidin-7-yl]-pyrrolidine-1,2-dicarboxylic acid 1-tert-butyl ester is dissolved in 4 ml of tetrahydrofuran; 10 ml of 4M hydrogen chloride in diethyl ether are added, and stirring is carried out for 1 hour at room temperature. The product is filtered off and dried under a high vacuum. The dihydrochloride of the title compound is obtained. 1 H-NMR (CD3 OD, ppm): 8.4 (s, 1H); 7.60 (s, 1H), 7.5-7.10 (m, 9H), 5.65 (m, 1H), 5.18 (s, 2H), 4.32 (m, 1H), 4.00-3.65 (m, 4H), 2.60 (m, 2H).

EXAMPLE 24

(2R/4S)-4-(4-Amino-5-phenyl-pyrrolo[2,3-d]pyrimidin-7-yl)-1-(2,2-dimethyl-propionyl)-pyrrolidine-2-carboxylic acid ethyl ester 0.130 g of (2R/4S)-4-(4-amino-5-(4-benzyloxycarbonylamino-5-phenyl-pyrrolo[2,3-d]pyrimidin-7-yl)-1-(2,2-dimethyl-propionyl)-pyrrolidine-2-carboxylic acid ethyl ester is dissolved in 8 ml of methanol, and the solution is hydrogenated over 0.030 g of palladium-on-carbon (10%) for 1 hour at normal pressure. The catalyst is removed by filtration, the filtrate is concentrated by

| | A | B | C |
|---|---|---|---|
| 1 | Name | Error | ID |
| 2 | karoline | ERROR:Parse error. Long unknown: karoline | http://appft1.uspto.gov/netacgi/nph-Parse |
| 3 | acyloxy | ERROR:Parse error. Long unknown: acyloxy | http://appft1.uspto.gov/netacgi/nph-Parse |
| 4 | alkylcarboxamide | ERROR:Structure cannot be generated for n | http://appft1.uspto.gov/netacgi/nph-Parse |
| 5 | alkylthiocarboxamide | ERROR:Structure cannot be generated for n | http://appft1.uspto.gov/netacgi/nph-Parse |
| 6 | alkylsulfonamide | ERROR:Structure cannot be generated for n | http://appft1.uspto.gov/netacgi/nph-Parse |
| 7 | alkylsulfinyl | ERROR:Structure cannot be generated for n | http://appft1.uspto.gov/netacgi/nph-Parse |
| 8 | alkylsulfonyl | ERROR:Structure cannot be generated for n | http://appft1.uspto.gov/netacgi/nph-Parse |
| 9 | alkylthio | ERROR:Structure cannot be generated for n | http://appft1.uspto.gov/netacgi/nph-Parse |
| 10 | alkylthioureyl | ERROR:Parse error. Long unknown: alkylthic | http://appft1.uspto.gov/netacgi/nph-Parse |
| 11 | alkylamino | ERROR:Structure cannot be generated for n | http://appft1.uspto.gov/netacgi/nph-Parse |
| 12 | dialkylamino | ERROR:Structure cannot be generated for n | http://appft1.uspto.gov/netacgi/nph-Parse |
| 13 | carboxamide | ERROR:failure | http://appft1.uspto.gov/netacgi/nph-Parse |
| 14 | diacylamino | ERROR:Parse error. Long unknown: diacyla | http://appft1.uspto.gov/netacgi/nph-Parse |
| 15 | dialkylcarboxamide | ERROR:Structure cannot be generated for n | http://appft1.uspto.gov/netacgi/nph-Parse |
| 16 | dialkylthiocarboxamide | ERROR:Structure cannot be generated for n | http://appft1.uspto.gov/netacgi/nph-Parse |
| 17 | dialkylsulfonamide | ERROR:Structure cannot be generated for n | http://appft1.uspto.gov/netacgi/nph-Parse |
| 18 | dialkylsulfonylamino | ERROR:Structure cannot be generated for n | http://appft1.uspto.gov/netacgi/nph-Parse |
| 19 | haloalkylcarboxamide | ERROR:Parse error. Long unknown: haloalky | http://appft1.uspto.gov/netacgi/nph-Parse |
| 20 | haloalkylsulfinyl | ERROR:Parse error. Long unknown: haloalky | http://appft1.uspto.gov/netacgi/nph-Parse |
| 21 | haloalkylsulfonyl | ERROR:Parse error. Long unknown: haloalky | http://appft1.uspto.gov/netacgi/nph-Parse |
| 22 | haloalkylthio | ERROR:Parse error. Long unknown: haloalky | http://appft1.uspto.gov/netacgi/nph-Parse |

Figure 6

CHEMICAL WEB BROWSER

FIELD OF THE INVENTION

This disclosure relates to identification of complex chemicals in text and display of the corresponding chemical structures.

BACKGROUND OF THE INVENTION

The ability to visualize chemical structures within a document would be useful for a technical person. For example, technical documents such as patents, papers, journal articles, etc., often list chemical names that are more easily understood when viewed as chemical structures. However, no convenient system exists which allows a user to be shown a chemical structure of a chemical name in the body of a text containing complex chemical formulae.

SUMMARY OF THE INVENTION

The present invention relates to a system, method and program product for a chemical web browser. In one embodiment there is a chemical web browser including a document management system for obtaining a document containing at least one chemical name. A chemical annotation system identifies the at least one chemical name in the document. A chemical formulae conversion system associates a chemical structure with the identified chemical name. The chemical structure is displayed.

In a second embodiment a chemical formula presentation method is presented. A document is accessed, the document containing at least one chemical name. The document is annotated to identify the at least one chemical name and the chemical name is associated with a chemical structure. The chemical structure is displayed.

In a third embodiment a computer program product is provided. The computer program product, when stored on computer readable storage medium and executed by a computer, performs the functions, including accessing a document containing at least one chemical name, annotating the document to identify the at least one chemical name, associating a chemical structure with the at least one chemical name and displaying the chemical structure.

In a fourth embodiment a method for deploying a chemical web browser system is provided. The method includes providing a document system for obtaining and displaying a document containing at least one chemical name. The method further includes providing a chemical annotation system for identifying the at least one chemical name in the document. A chemical formulae conversion system associates a chemical structure with the identified chemical name wherein the chemical structure is displayed.

BRIEF DESCRIPTION OF THE DRAWINGS

These and other features of this invention will be more readily understood from the following detailed description of the various aspects of the invention taken in conjunction with the accompanying drawings.

FIG. 2 depicts chemical rich text in a document in accordance with an embodiment of the present invention.

FIG. 3 depicts a screen shot of chemical rich text in accordance with the embodiment of the invention.

FIG. 5 depicts a spreadsheet in a chemical web browser containing chemical names, structures, molecular weights and url references in accordance with the embodiment of the invention.

FIG. 6 depicts a spreadsheet having chemical names that cannot be associated with a valid chemical structure in accordance with the embodiment of the invention.

Figure 1:
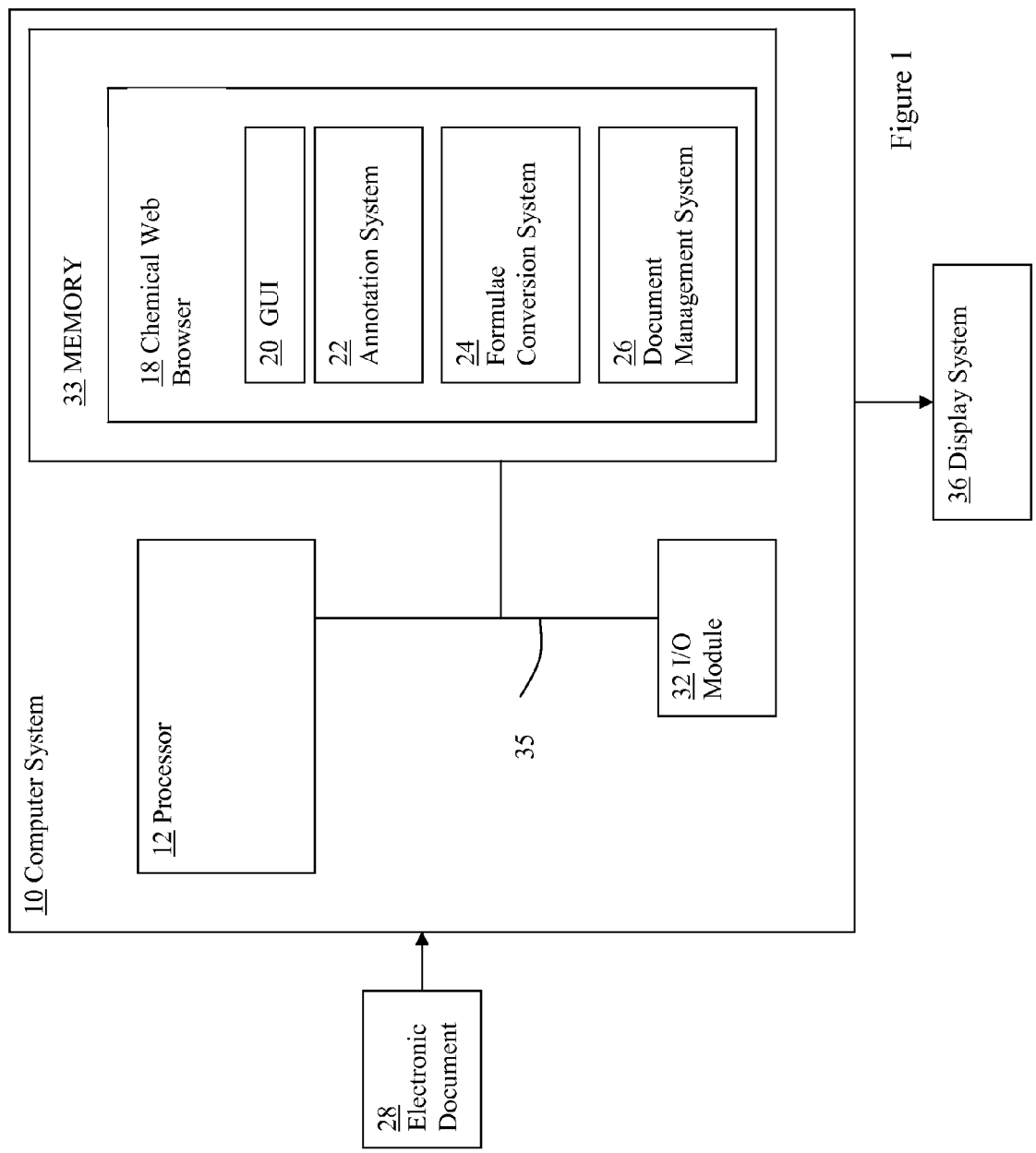
FIG. 1 is a schematic diagram of a computer system in accordance with an embodiment of the invention.

The drawings are merely schematic representations not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

FIG. 1 depicts a computer system 10 having a chemical web browser 18 for processing an electronic document 28 that contains one or more chemical names. Chemical web browser 18 generally includes: a graphical user interface (GUI) 20 for displaying the electronic document and associated chemical structures; an annotation system 22 for identifying chemical names within the electronic document; a formulae conversion system 24 for converting chemical names to structures; and a document management system 26 for importing and storing documents.

A GUI is a way for humans to interact with a computer that uses windows, icons, and menus, and can be manipulated by a mouse, trackball, touchpad, etc., and often to a limited extent a keyboard as well. Commands are issued in the GUI by using a mouse, trackball or touchpad to first move a pointer on the screen to, or on top of, the icon, menu item, or window of interest in order to select that object. Then, for example, icons and windows can be moved by dragging (moving the mouse with the held down) and objects or programs can be opened by clicking on their icons.

Annotation system 22 parses an electronic document to identify chemical names in the document. The annotation system 22 may utilize any technique or system to review the document and identify all chemical names residing therein. For example, terms may be cross-referenced with a database of known chemical names.

Conversion system 24 converts a chemical name identified by annotation systems 22 to a chemical structure. Such conversions may be done using software. For instance, SMILES™ (Simplified Line Input Molecular Entry Specification) refers to a line notation for encoding molecular structures. Algorithms have been developed to ensure the same SMILES™ string is generated for a molecule regardless of the order of atoms in the structure. Algorithms for generating SMILES™ strings have been developed at Daylight Chemical Information Systems, OpenEye Scientific Software and Chemical Computing Group.

Document management system 26 imports and stores electronic documents from various sources. The management system 26 can import documents found on the web, or any network or storage device. The document management system imports 26 documents of any format including pdf, HTML, WORD, etc.

Display system 36 includes any type of display, for example monitors, hand held devices, printers, phones, etc.

Figure 3:
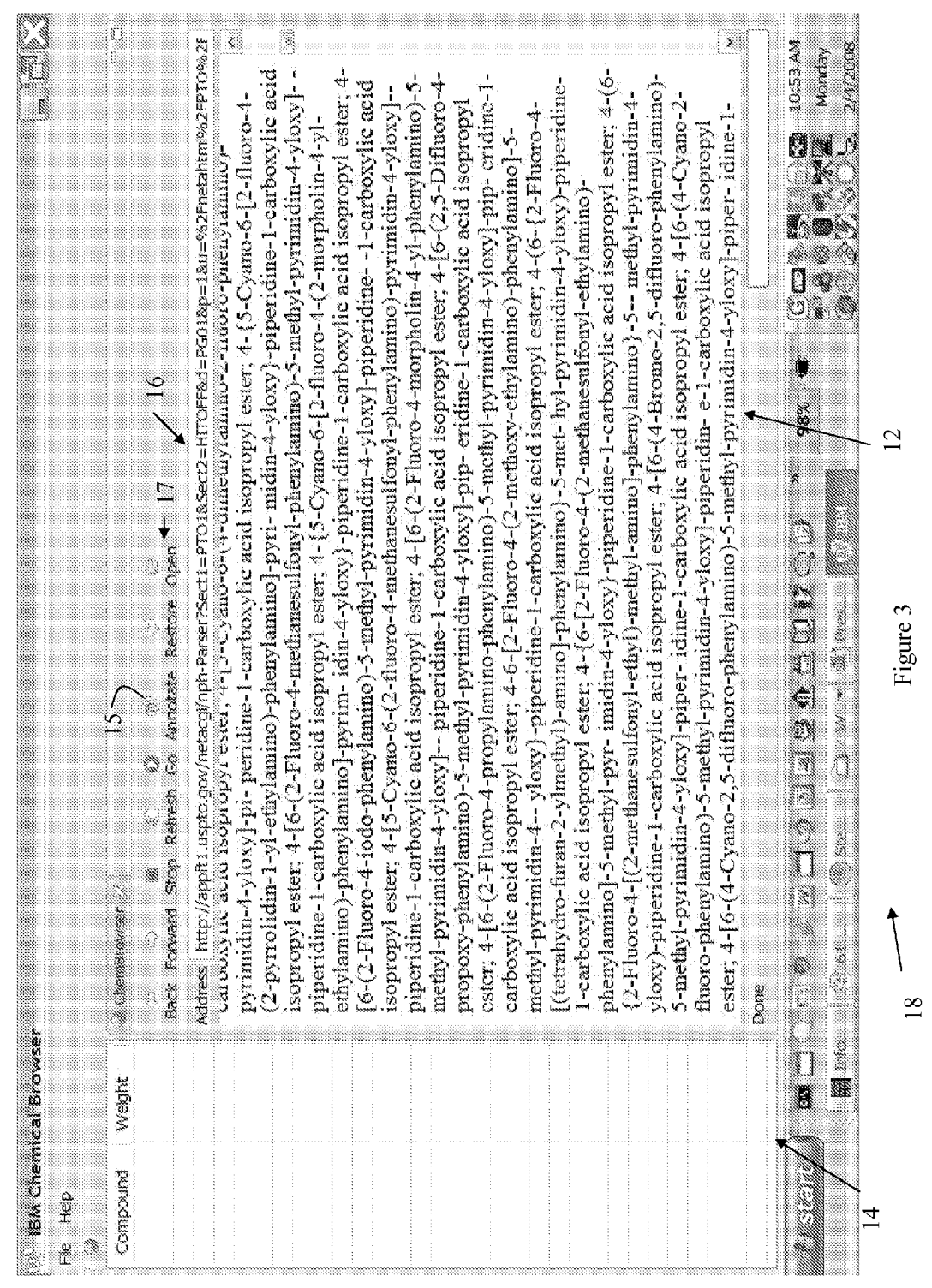
Figure 4:
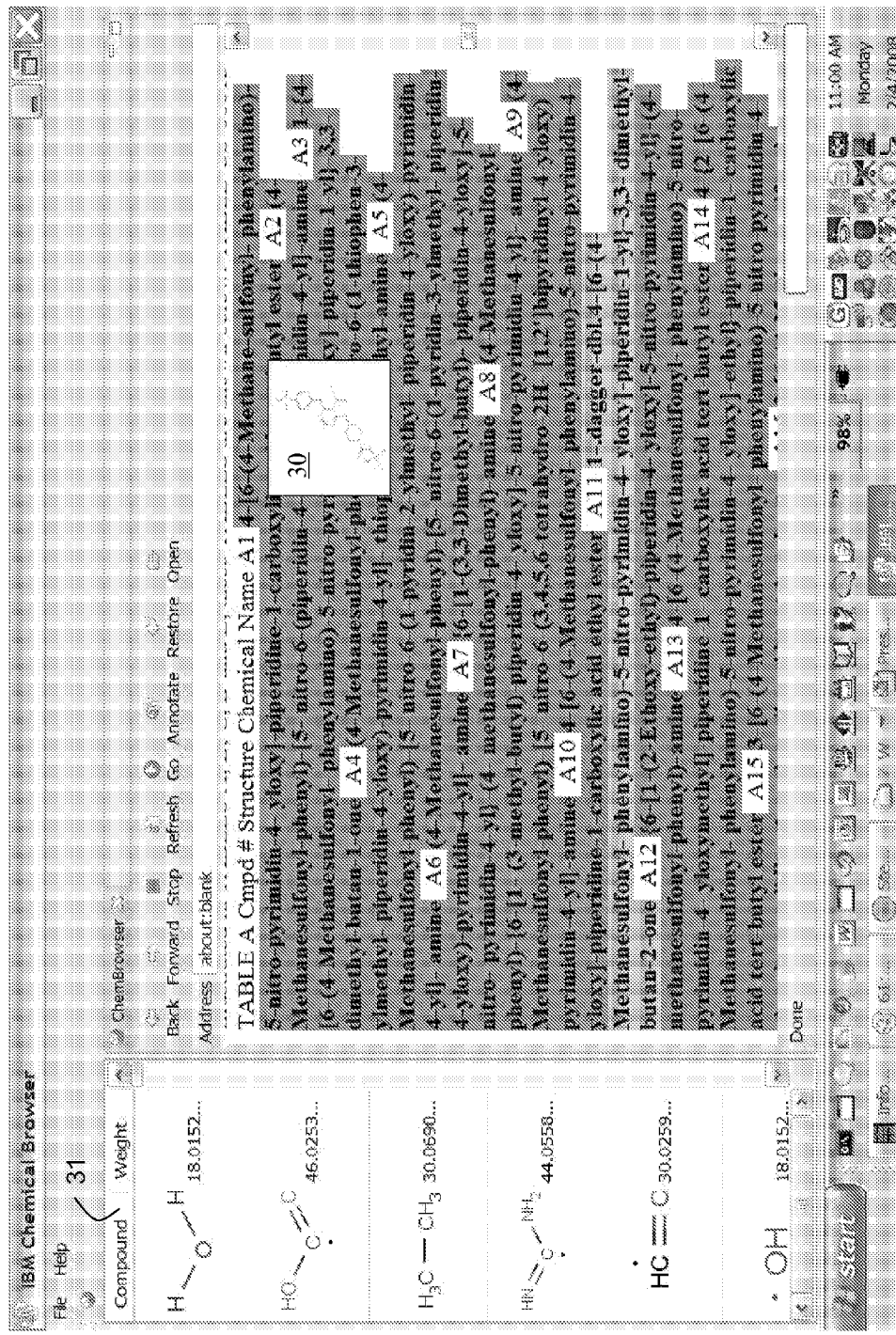
FIG. 4 depicts a screen shot of annotated chemical rich text in a chemical web browser in accordance with the embodiment of the invention.

An example of the chemical web browser 18 and how it works is described in detail below. FIGS. 3 and 4 show the chemical web browser as it performs selected functions input from the GUI.

Referring to FIG. 2, a document containing numerous chemical names is shown. The key molecules and their respective structures are not apparent from the document. Even for a skilled artisan, the structure of the chemical is not readily apparent. For example, the chemical name in the first two lines of FIG. 2 is (2P/4S)-4-[4-Amino-5-(4-benzyloxy-phenyl)pyrrolo[2,3-d]pyrimidin-7-yl]-2-hydroxymethyl-pyrrolidine-1-carboxylic acid tert-butyl ester. The chemical structure associated with the chemical name would be more useful information to the reader of the document in most situations.

FIG. 3 shows a screen shot of an embodiment of chemical web browser 18. Chemical web browser 18 generally includes a first window 12 for displaying an electronic document containing at least one chemical name; a second window 14 for displaying chemical structures; a third window 16 for displaying an address (such as a web address) of the electronic document containing at least one chemical name; and a tool bar 17 containing a set of user selectable tools.

In this example, a chemical rich document is displayed in the first window 12 and contains a series of the chemical names, similar to FIG. 2. In order to view structures associated with each of the chemical names in the document, a user selects the annotate button 15 on the tool bar 17 of the chemical web browser 18. Annotation system 22 (FIG. 1) parses the document and identifies all chemical names residing therein.

Annotation system 22 uses naming rules to identify and recognize chemical names within a document. After annotation of the document, the web browser 18 associates a chemical structure with each identified chemical name. After annotation, each identified chemical name is identified by an alphanumeric character as shown in FIG. 4. In FIG. 4, chemical names A1 through A15 are identified within the document. In FIG. 4, the highlighted chemical name is A11 or 1-.dagger-dbl.4-[6-(4Methanesulfonyl-phenylamino)-5-nitro-pyrimidin-4-yloxy]-piperidin}-3,3-dimethyl-butan-2-one. This is shown by the structure 30. The GUI 20 is used to select or highlight a chemical name(s), in this example A11, by "mousing" over or some other known fashion. The chemical structure is displayed in 30.

In addition to showing the selected chemical structure from the displayed document, a spreadsheet is displayed in window 14, identified generally as 31. Although not shown, window 14 may include an alphanumeric column for easy reference back to window 12. Every chemical structure in the annotated document is automatically loaded into the spreadsheet 31 at the side of the display together with the respective molecular weight.

FIG. 4 shows a table or spreadsheet in window 14 and the table or spreadsheet can be sorted by molecular weight of the compound. This can be accomplished by clicking on or otherwise selecting the molecular weight attribute. In addition, one can scroll through the content of the spreadsheet and click or otherwise select a compound and the section in the document that contains the text is displayed.

Figure 5:
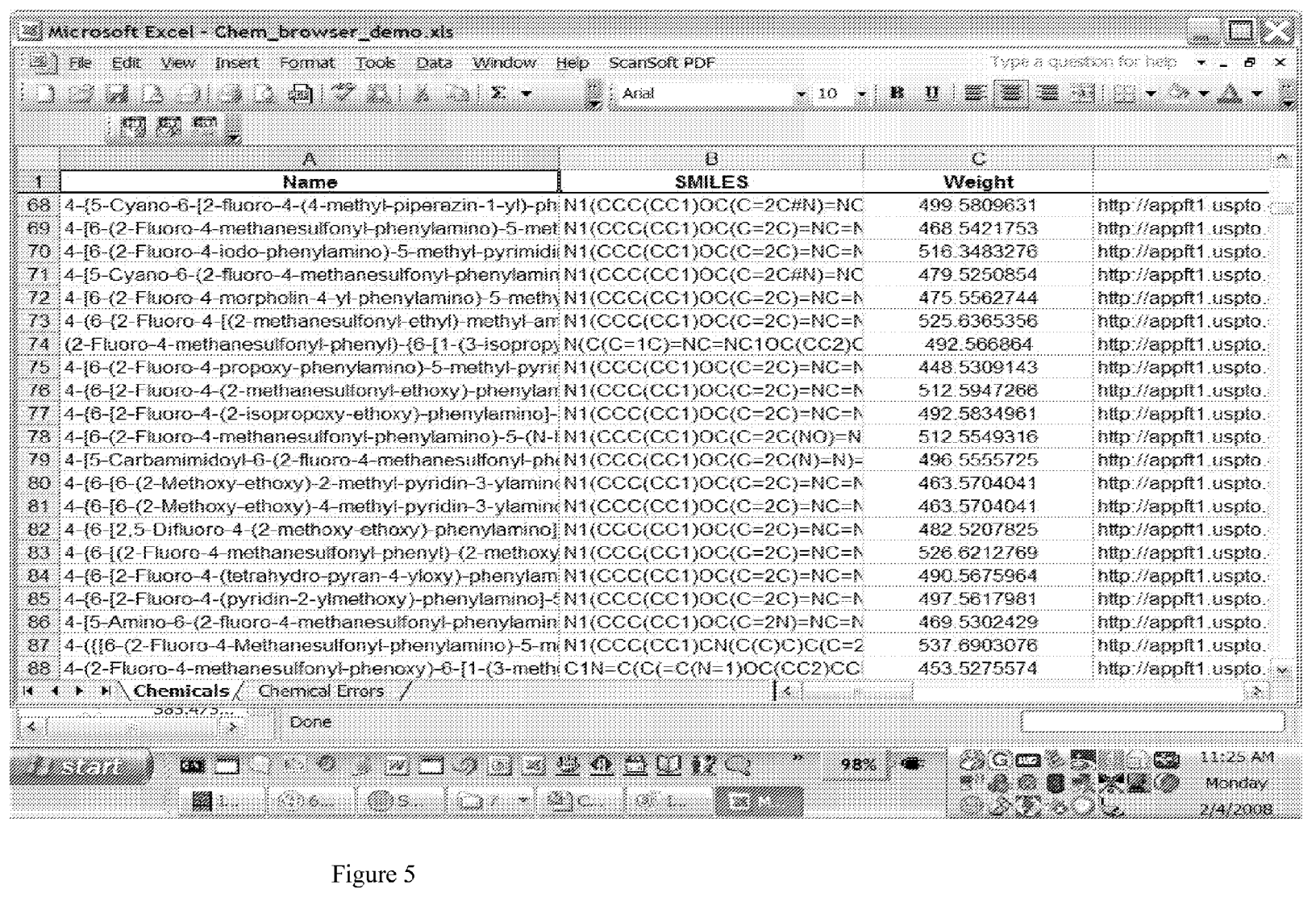

The spreadsheet can be saved as a unique document containing the chemical names, chemical structures, molecular weight and url references. Such a spreadsheet is shown in FIG. 5. FIG. 6 contains a spreadsheet of chemical names identified but not converted to valid structures. This occurs when the chemical name is not a valid chemical structure. This spreadsheet can be accessed through the error tabs at the bottom of the screenshot of FIG. 5.

Figure 7:
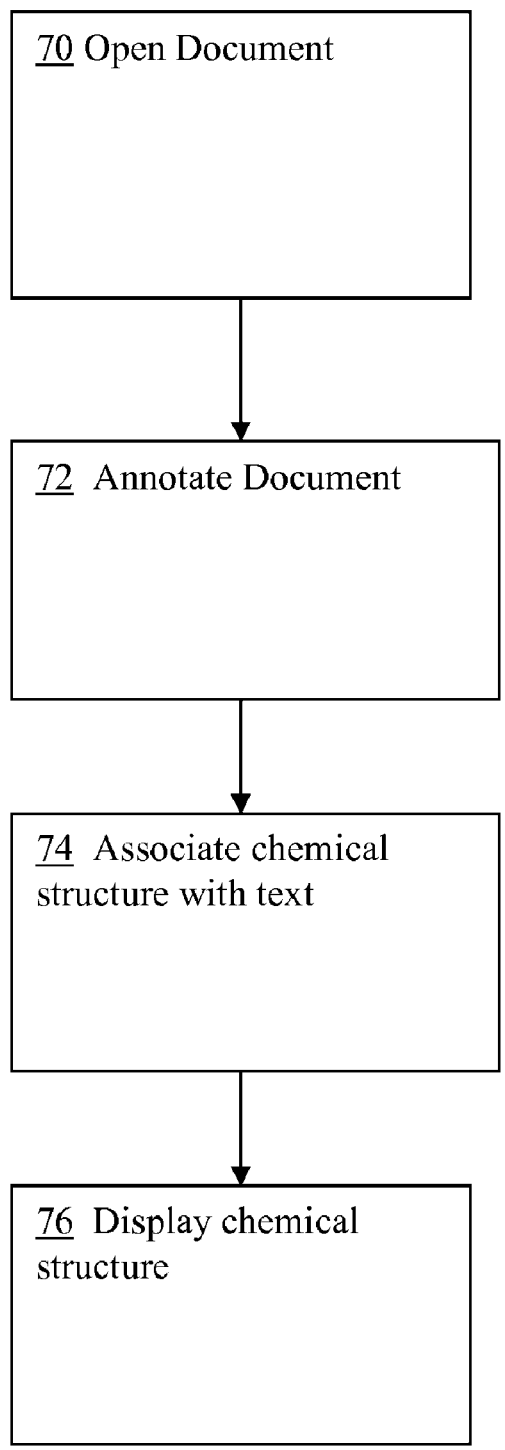
FIG. 7 depicts a flowchart showing an aspect of the invention.

FIG. 7 shows a flow diagram depicting a method of an embodiment of the invention. In a first step 70, an electronic document 28 (FIG. 1) is accessed through I/O module 32 (FIG. 1) or through document management system 26 (FIG. 1) where the document had been previously stored. The document is annotated in next step shown as 72. Annotation step processes the document to identify chemical names. Step 74 associates each chemical name with its respective chemical structure. The chemical structure is displayed in block 76.

Referring to FIG. 1, it is understood that chemical web browser 18 may be implemented as any type of computing system 10 or device. Such a computing system generally includes a processor or CPU 11, input/output (I/O) 32, memory 33, and a bus 35. The processor may comprise a single processing unit, or be distributed across one or more processing units in one or more locations, e.g., on a client and server. Memory may comprise any known type of data storage, including magnetic media, optical media, random access memory (RAM), read-only memory (ROM), a data cache, a data object, etc. Moreover, memory 33 may reside at a single physical location, comprising one or more types of data storage, or be distributed across a plurality of physical systems in various forms. A data warehouse for holding data may likewise reside at a single physical location, comprising one or more types of data storage, or be distributed across a plurality of physical systems in various forms.

I/O may comprise any system for exchanging information to/from an external resource. External devices/resources may comprise any known type of external device, including a monitor/display, speakers, storage, another computer system, a hand-held device, keyboard, mouse, voice recognition system, speech output system, printer, facsimile, pager, etc. A bus 35 provides a communication link between each of the components in the computer system and likewise may comprise any known type of transmission link, including electrical, optical, wireless, etc. Although not shown, additional components, such as cache memory, communication systems, system software, etc., may be incorporated into computer system.

Access to the computer system may be provided over a network such as the Internet, a local area network (LAN), a wide area network (WAN), a virtual private network (VPN), etc. Communication could occur via a direct hardwired connection (e.g., serial port), or via an addressable connection that may utilize any combination of wireline and/or wireless transmission methods. Moreover, conventional network connectivity, such as Token Ring, Ethernet, WiFi or other conventional communications standards could be used. Still yet, connectivity could be provided by conventional TCP/IP sockets-based protocol. In this instance, an Internet service provider could be used to establish interconnectivity. Further, as indicated above, communication could occur in a client-server or server-server environment.

It should be appreciated that the teachings of the present invention could be offered as a business method on a subscription or fee basis. For example, a computer system comprising a chemical web browser system 18 could be created, maintained and/or deployed by a service provider that offers the functions described herein for customers. That is, a service provider could offer to deploy or provide the ability to map feature vectors as described above.

It is understood that in addition to being implemented as a system and method, the features may be provided as a program product stored on a computer-readable medium, which when executed, enables a computer system to provide a chemical web browsing functions. To this extent, the computer-readable medium may include program code, which implements the processes and systems described herein. It is understood that the term "computer-readable medium" comprises one or more of any type of physical embodiment of the program code. In particular, the computer-readable storage medium can comprise program code embodied on one or more portable storage articles of manufacture (e.g., a compact disc, a magnetic disk, a tape, etc.), on one or more data storage portions of a computing device, such as memory and/or a storage system.

As used herein, it is understood that the terms "program code" and "computer program code" are synonymous and mean any expression, in any language, code or notation, of a set of instructions that cause a computing device having an information processing capability to perform a particular function either directly or after any combination of the following: (a) conversion to another language, code or notation; (b) reproduction in a different material form; and/or (c) decompression. To this extent, program code can be embodied as one or more types of program products, such as an application/software program, component software/a library of functions, an operating system, a basic I/O system/driver for a particular computing and/or I/O device, and the like. Further, it is understood that terms such as "component" and "system" are synonymous as used herein and represent any combination of hardware and/or software capable of performing some function(s).

The block diagrams in the figures illustrate the architecture, functionality, and operation of possible implementations of systems, methods and computer program products according to various embodiments of the present invention. In this regard, each block in the block diagrams may represent a module, segment, or portion of code, which comprises one or more executable instructions for implementing the specified logical function(s). It should also be noted that the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams can be implemented by special purpose hardware-based systems which perform the specified functions or acts, or combinations of special purpose hardware and computer instructions.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. A chemical web browser, executed on at least one computing device, the chemical web browser comprising:
    a document management system for obtaining a document containing at least one chemical name, using the at least one computing device;
    a chemical annotation system for identifying the at least one chemical name contained within the document;
    a formulae conversion system for associating a chemical structure with the identified chemical name; and
    a display system for:
        displaying the chemical structure proximate to the identified chemical name from the document in the chemical web browser in response to selection of an annotate button displayed in the chemical web browser; and
        displaying an alphanumeric character proximate to the identified chemical name in the chemical web browser in response to the selection of the annotate button displayed in the chemical web browser.

2. The chemical web browser of claim 1, wherein the document management system displays the chemical structure in a spreadsheet.

3. The chemical web browser of claim 1, wherein the chemical annotation system determines the molecular weight of the chemical structure.

4. The chemical web browser of claim 3, wherein the display system further displays the molecular weight of the chemical structure proximate to the identified chemical name.

5. The chemical web browser of claim 1, wherein the at least one chemical name in the document is highlighted in the document.

6. The chemical web browser of claim 1, wherein the formulae conversion system determines whether the at least one chemical name in the text is convertible to a valid chemical structure.

7. The chemical web browser of claim 6, wherein the document management system issues an error message when the at least one chemical name is not convertible to a valid chemical structure.

8. A method comprising:
    presenting a chemical formula using a computer device configured to perform the following:
        accessing a document containing at least one chemical name;
        annotating the document to identify the at least one chemical name;
        associating a chemical structure with the identified at least one chemical name;
        displaying the chemical structure proximate to the identified at least one chemical name from the document in a chemical web browser in response to selection of an annotate button displayed in the chemical web browser; and
        displaying an alphanumeric character proximate to the identified chemical name in the chemical web browser in response to the selection of the annotate button displayed in the chemical web browser.

9. The method of claim 8, further comprising determining the molecular weight of the chemical structure.

10. The method of claim 8, further comprising highlighting the at least one chemical name in the document.

11. A computer program product comprising:
    program code stored on computer readable storage medium, which when executed by a computer, performs the functions comprising:
        accessing a document containing at least one chemical name;
        annotating the document to identify the at least one chemical name;
        associating a chemical structure with the identified at least one chemical name;
        displaying the chemical structure proximate to the identified at least one chemical name from the document in a chemical web browser in response to selection of an annotate button displayed in the chemical web browser; and
        displaying an alphanumeric character proximate to the identified chemical name in the chemical web browser in response to the selection of the annotate button displayed in the chemical web browser.

12. The computer program product of claim 11, further comprising program code for determining a molecular weight of the chemical structure.

13. The computer program product of claim 12, further comprising program code for displaying the molecular weight of the chemical structure proximate to the identified at least one chemical name from the document.

14. The computer program product of claim 11, further comprising program code for highlighting the at least one chemical name in the document.

15. The computer program product of claim 11, further comprising program code for determining whether the at least one chemical name in the text is convertible to a valid chemical structure.

16. The computer program product of claim 15, further comprising displaying an error when the al least one chemical name is not convertible to a valid chemical structure.

17. A method for deploying a chemical web browser system, the method comprising:
    providing computer system, including the chemical web browser;
    providing a document system for obtaining and displaying a document containing at least one chemical name; and
    providing a chemical annotation system for identifying the at least one chemical name and associating a chemical structure with the identified chemical name,
    wherein the document system displays the chemical structure proximate to the identified chemical name from the document in the chemical web browser in response to selection of an annotate button displayed in the chemical web browser, and
    wherein the document system displays an alphanumeric character proximate to the identified chemical name in the chemical web browser in response to the selection of the annotate button displayed in the chemical web browser.

18. The method of claim 17, wherein the chemical annotation system highlights the at least one chemical name in the document.

19. The method of claim 17, wherein the chemical annotation system determines whether the at least one chemical name in the text is convertible to a valid chemical structure.

20. The method of claim 19, wherein the document system displays an error when the al least one chemical name is not convertible to a valid chemical structure.

\* \* \* \* \*